United States Patent [19]
Reichard et al.

[11] Patent Number: 5,789,422
[45] Date of Patent: Aug. 4, 1998

[54] SUBSTITUTED ARYLALKYLAMINES AS NEUROKININ ANTAGONISTS

[75] Inventors: Gregory A. Reichard, Parsippany; Robert G. Aslanian, Rockaway, both of N.J.

[73] Assignee: Schering Corporation, Kenilworth, N.J.

[21] Appl. No.: 742,606

[22] Filed: Oct. 28, 1996

[51] Int. Cl.$^6$ .................. A61K 31/445; C07D 211/22
[52] U.S. Cl. .................. 514/327; 514/252; 514/255; 514/318; 514/319; 514/323; 514/324; 514/329; 514/330; 514/331; 544/336; 544/405; 544/408; 544/409; 546/188; 546/193; 546/194; 546/201; 546/207; 546/208; 546/209; 546/214; 546/217; 546/221; 546/225; 546/228; 546/229; 546/231; 546/324; 546/331
[58] Field of Search .................. 544/336, 405, 544/408, 409; 546/188, 193, 194, 201, 207, 208, 209, 214, 217, 221, 225, 228, 229, 231, 234, 331; 514/252, 255, 318, 319, 323, 324, 327, 329, 330, 331

[56] References Cited

U.S. PATENT DOCUMENTS

| | | | |
|---|---|---|---|
| 5,236,921 | 8/1993 | Emonds-alt et al. | 514/252 |
| 5,350,852 | 9/1994 | Emonds-Alt et al. | |
| 5,534,525 | 7/1996 | Miller | 514/316 |

FOREIGN PATENT DOCUMENTS

| | | |
|---|---|---|
| 14909/95 | 9/1995 | Australia . |
| 630887 | 12/1994 | European Pat. Off. . |
| 0 680 962 | 11/1995 | European Pat. Off. . |
| 0 699 674 | 3/1996 | European Pat. Off. . |
| 714891 | 5/1996 | European Pat. Off. . |
| 2717802 | 9/1995 | France . |
| 2274777 | 8/1994 | United Kingdom . |
| 93/01160 | 1/1993 | WIPO . |
| 93/01169 | 1/1993 | WIPO . |
| 93/23380 | 11/1993 | WIPO . |
| 94/10146 | 5/1994 | WIPO . |
| 94/20500 | 9/1994 | WIPO . |
| 94/29309 | 12/1994 | WIPO . |
| 95/05377 | 2/1995 | WIPO . |
| 95/12577 | 5/1995 | WIPO . |

OTHER PUBLICATIONS

Maggi et al, *Eur. J. Pharmacol.*, 166, (1989), pp. 435–440.
Ellis et al, *J. Pharmacol. Exp. Ther.*, 267, 1 (1993), pp. 95–101.
Furchgott, *Pharm. Rev.*, 7 (1955), pp. 183–265.
Arunlakshana et al, *Brit. J. Pharmacol.*, 14, 48 (1959), pp. 48–58.
Danko et al, *Pharmacol. Comm.*, 1, 3 (1992), pp. 203–209.
Chung et al, *Molecular Pharmacol.*, 48 (1995), pp. 711–716.
Abstract of FR 2,717,802.

Primary Examiner—Ceila Chang
Attorney, Agent, or Firm—Anita W. Magatti

[57] ABSTRACT

Compounds represented by the structural formula

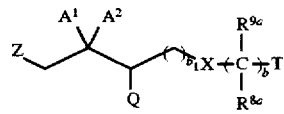

or a pharmaceutically acceptable salt thereof are disclosed, wherein:

$A^1$ is —$CH_2R^6$, —$OR^6$, —$N(R^6)(R^7)$, —$S(O)_eR^{13}$, —$(C(R^6)(R^7))_{1-6}$—$OR^6$, —$(C(R^6)(R^7))_{1-6}$—$N(R^6)(R^7)$ or —$(C(R^6)(R^7))_{1-6}$—$S(O)_eR^{13}$ and $A^2$ is H, or $A^1$ and $A^2$ together are =O, =$C(R^6)(R^7)$, =$NOR^6$ or =S;

Q is phenyl, naphthyl, —$SR^6$, —$N(R^6)(R^7)$, —$OR^6$ or heteroaryl;

T is H, aryl, heterocycloalkyl, heteroaryl, cycloalkyl or bridged cycloalkyl;

b is 0, 1 or 2;

$b_1$ is 1 or 2;

X is a bond, —C(O)—, —O—, —$NR^6$—, —$S(O)_e$—, —$N(R^6)C(O)$—, —$C(O)N(R^6)$—, —$OC(O)NR^6$—, —$OC(=S)NR^6$—, —$N(R^6)C(=S)O$—, —$C(=NOR^6)$—, —$S(O)_2N(R^6)$—, —$N(R^6)S(O)_2$—, —$N(R^6)C(O)O$— or —OC(O)—;

$R^6$, $R^7$, $R^{8a}$, and $R^{13}$ are H, alkyl, hydroxyalkyl, alkoxyalkyl, phenyl or benzyl; or $R^6$ and $R^7$, together with the nitrogen to which they are attached, form a ring;

$R^9$ and $R^{9a}$ independently are $R^6$ or —$OR^6$;

Z is optionally substituted

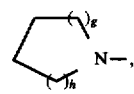

wherein g is 0–3 and h is 1–4, provided the sum of h and g is 1–7;

wherein the aryl, phenyl, benzyl, naphthyl, heterocycloalkyl and heteroaryl groups are optionally substituted. Methods of treating asthma, cough, bronchospasm, imflammatory diseases, and gastrointestinal disorders with said compounds, and pharmaceutical compositions comprising said compounds are disclosed.

12 Claims, No Drawings

SUBSTITUTED ARYLALKYLAMINES AS NEUROKININ ANTAGONISTS

BACKGROUND OF THE INVENTION

The present invention relates to a genus of substituted arylalkylamines useful as antagonists of tachykinin receptors, in particular as antagonists of the neuropeptides neurokinin-1 receptor ($NK_1$) and/or neurokinin-2 receptor ($NK_2$) and/or neurokinin-3 receptor ($NK_3$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, central nervous system conditions such as migraine and epilepsy, nociception, and various gastrointestinal disorders such as Crohn—s disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Some $NK_1$ and $NK_2$ receptor antagonists have previously been disclosed: arylalkylamines were disclosed in U.S. Pat. No. 5,350,852, issued Sep. 27, 1994, and spiro-substituted azacycles were disclosed in WO 94/29309, published Dec. 22, 1994.

SUMMARY OF THE INVENTION

Compounds of the present invention are represented by the formula I

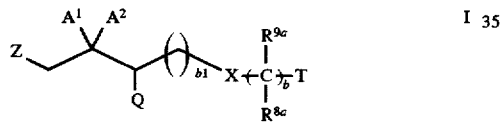

or a pharmaceutically acceptable salt thereof, wherein:

$A^1$ is —$CH_2R^6$, —$OR^6$, —$N(R^6)(R^7)$, —$S(O)_eR^{13}$, —($C(R^6)(R^7))_{1-6}$—$OR^6$, —($C(R^6)(R^7))_{1-6}$—$N(R^6)(R^7)$ or —($C(R^6)(R^7))_{1-6}$—$S(O)_eR^{13}$ and $A^2$ is H, or $A^1$ and $A^2$ together are =O, =$C(R^6)(R^7)$, =$NOR^6$ or =S;

Q is $R^5$-phenyl, $R^5$-naphthyl, —$SR^6$, —$N(R^6)(R^7)$, —$OR^6$ or $R^5$-heteroaryl;

T is H, $R^4$-aryl, $R^4$-heterocycloalkyl, $R^4$-heteroaryl, $R^4$-cycloalkyl or $R^{10}$-bridged cycloalkyl;

b is 0, 1 or 2;

$b_1$ is 1 or 2;

X is a bond, —C(O)—, —O—, —$NR^6$—, —$S(O)_e$—, —$N(R^6)C(O)$—, —$C(O)N(R^6)$—, —$OC(O)NR^6$—, —$OC(=S)NR^6$—, —$N(R^6)C(=S)O$—, —$C(=NOR^6)$—, —$S(O)_2N(R^6)$—, —$N(R^6)S(O)_2$—, —$N(R^6)C(O)O$— or —$OC(O)$—;

$R^4$ and $R^5$ are independently 1-3 substituents independently selected from the group consisting of H, halogeno, —$OR^6$, —$OC(O)R^6$, —$OC(O)N(R^6)(R^7)$, —$N(R^6)(R^7)$, $C_{1-6}$ alkyl, —$CF_3$, —$C_2F_5$, —$COR^6$, —$CO_2R^6$, —$CON(R^6)(R^7)$, —$S(O)_eR^{13}$, —CN, —$OCF_3$, —$NR^6CO_2R^{16}$, —$NR^6COR^7$, —$NR^8CON(R^6)(R^7)$, $R^{15}$-phenyl, $R^{15}$-benzyl, $NO_2$, —$N(R^6)S(O)_2R^{13}$ or —$S(O)_2N(R^6)(R^7)$; or adjacent $R^4$ substituents or adjacent $R^5$ substituents can form a —O—$CH_2$—O— group; and $R^4$ can also be $R^{15}$-heteroaryl;

$R^6$, $R^7$, $R^8$, $R^{8a}$, and $R^{13}$ are independently selected from the group consisting of H, $C_{1-6}$ alkyl, $C_2$-$C_6$ hydroxyalkyl, $C_1$-$C_6$ alkoxy-$C_1$-$C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of —O—, —S— and —$N(R^{19})$—;

$R^9$ and $R^{9a}$ are independently selected from the group consisting of $R^6$ and —$OR^6$, provided that when $R^9$ is OH, X is a bond, —C(O)—, —$N(R^6)C(O)$— or —$C(=NOR^6)$—;

$R^{10}$ is independently selected from the group consisting of H and $C_{1-6}$ alkyl;

$R^{15}$ is 1 to 3 substituents independently selected from the group consisting of H, $C_1$-$C_6$ alkyl, $C_1$-$C_6$ alkoxy, $C_1$-$C_6$ alkylthio, halogeno, —$CF_3$, —$C_2F_5$, —$COR^{10}$, —$CO_2R^{10}$, —$C(O)N(R^{10})_2$, —$S(O)_eR^{10}$, —CN, —$N(R^{10})COR^{10}$, —$N(R^{10})CON(R^{10})_2$ and —$NO_2$;

$R^{16}$ is $C_{1-6}$ alkyl, $R^{15}$-phenyl or $R^{15}$-benzyl;

$R^{19}$ is H, $C_1$-$C_6$ alkyl, —$C(O)N(R^{10})_2$, —$CO_2R^{10}$, —$(C(R^8)(R^9))_f$—$CO_2R^{10}$ or —$(C(R^8)(R^9))_u$—$C(O)N(R^{10})_2$;

f is 1–6;

u is 0–6;

Z is

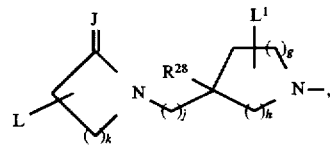

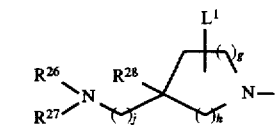

or

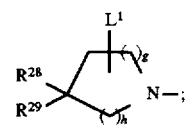

f is 1–6;

g and j are independently 0–3;

h and k are independently 1–4, provided the sum of h and g is 1–7;

J is two hydrogen atoms, =O, =S, =$NR^9$ or =$NOR^6$;

L and $L^1$ are independently selected from the group consisting of H, $C_1$-$C_6$ alkyl, $C_1$-$C_6$ alkenyl, —$CH_2$-cycloalkyl, $R^{15}$-benzyl, $R^{15}$-heteroaryl, —$C(O)R^6$, —$(CH_2)_m$—$OR^6$, —$(CH_2)_m$—$N(R^6)(R^7)$, —$(CH_2)_m$—$C(O)$—$OR^6$ and —$(CH_2)_m$—$C(O)N(R^6)(R^7)$;

m is 0 to 4, provided that when j is 0, m is 1–4;

$R^{25}$ is H, $C_1$-$C_6$ alkyl, —CN, $R^{15}$-phenyl or $R^{15}$-benzyl;

$R^{26}$ and $R^{27}$ are independently selected from the group consisting of H, $C_1$-$C_6$ alkyl, $R^4$-aryl and $R^4$-heteroaryl; or $R^{26}$ is H, $C_1$-$C_6$ alkyl, $R^4$-aryl or $R^4$-heteroaryl, and $R^{27}$ is —$C(O)R^6$, —$C(O)$—$N(R^6)(R^7)$, —$C(O)(R^4$-aryl), —$C(O)(R^4$-heteroaryl), —$SO_2R^{13}$ or —$SO_2$—($R^4$-aryl);

$R^{28}$ is H, —$(C(R^6)(R^{19}))_t$—G or —$(C(R^6)(R^7))_v$—$G^2$;

t and v are 0, 1, 2 or 3, provided that when j is 0, t is 1, 2 or 3;

$R^{29}$ is H, $C_1$-$C_6$ alkyl, —$C(R^{10})_2S(O)_eR^6$, $R^4$-phenyl or $R^4$-heteroaryl;

G is H, $R^4$-aryl, $R^4$-hetero-cycloalkyl, $R^4$-heteroaryl, $R^4$-cycloalkyl, —$OR^6$, —$N(R^6)(R^7)$, —$COR^6$, —$CO_2R^6$, —$CON(R^7)(R^9)$, —$S(O)_eR^{13}$, —$NR^6CO_2R^{16}$, —$NR^6COR^7$, —$NR^8CON(R^6)(R^7)$, —$N(R^6)S(O)_2R^{13}$, —S(O)$_2$N(R$^6$)(R$^7$), —OC(O)R$^6$, —OC(O)N(R$^6$)(R$^7$), —C(=NOR$^8$)N(R$^6$)(R$^7$), —C(=NR$^{25}$)N(R$^6$)(R$^7$), —N(R$^8$)C(=NR$^{25}$)N(R$^6$)(R$^7$), —CN, —C(O)N(R$^6$)OR$^7$ or —C(O)N(R$^9$)-(R$^4$-heteroaryl), provided that when n is 1 and u is 0, or when R$^9$ is —OR$^6$, G is not —OH or —N(R$^6$)(R$^7$); and G$^2$ is R$^4$-aryl, R$^4$-heterocycloalkyl, R$^4$-heteroaryl, R$^4$-cycloalkyl, —COR$^6$, —CO$_2$R$^{16}$, —S(O)$_2$N(R$^6$)(R$^7$) or —CON(R$^6$)(R$^7$).

Preferred are compounds of formula I wherein X is —O—, —NR$^6$—, —N(R$^6$)C(O)—, —OC(O)NR$^6$ or —N(R$^6$)C(O)O. More preferred are compounds of formula I wherein X is —NR$^6$— or —N(R$^6$)C(O)—. Also preferred are compounds wherein b is 0 or 1 when X is —NR$^6$— or —N(R$^6$)C(O)—. Also preferred are compounds wherein b$_1$ is 1. T is preferably R$^4$-aryl or R$^4$-heteroaryl, with R$^4$-aryl, especially R$^4$-phenyl, being more preferred. Also preferred are compounds wherein R$^{8a}$ and R$^{9a}$ are independently hydrogen, hydroxyalkyl or alkoxyalkyl, with hydrogen being more preferred. Especially preferred are compounds wherein R$^{8a}$ and R$^{9a}$ are each hydrogen, X is —NR$^6$— or —N(R$^6$)C(O)—, T is R$^4$-aryl and R$^4$ is two substituents selected from C$_1$–C$_6$ alkyl, halogeno, —CF$_3$ and C$_1$–C$_6$ alkoxy. When T is R$^4$-heteroaryl, a preferred definition includes R$^4$-pyridinyl.

Also preferred are compounds wherein Q is R$^5$-phenyl, R$_5$-naphthyl or R$^5$-heteroaryl; especially preferred definitions for Q are R$^5$-phenyl, wherein R$^5$ is preferably two halogeno substituents, and benzothienyl.

Preferred are compounds of formula I wherein A$^1$ is —OR$^6$, —N(R$^6$)(R$^7$), —S(O)$_e$R$^{13}$ or —(C(R$^6$)(R$^7$))$_{1-6}$—N(R$^6$)(R$^7$) and A$^2$ is H; also preferred compounds are where A$^1$ and A$^2$ together are =O, =C(R$^6$)(R$^7$) or =NOR$^6$.

Preferred definitions of Z are

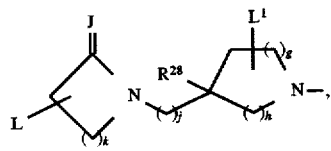

and

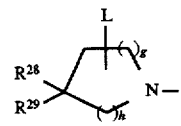

with the following groups being more preferred:

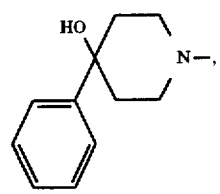

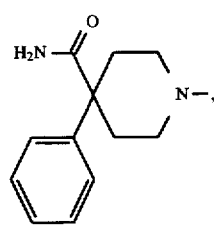

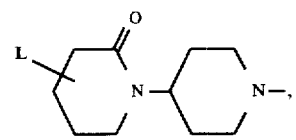

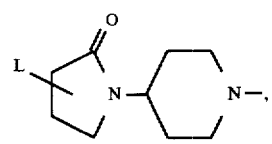

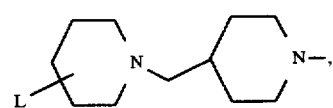

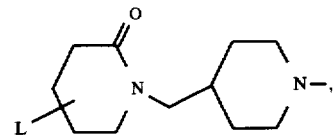

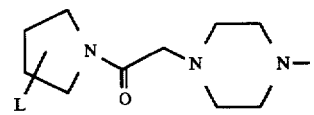

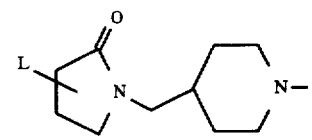

and

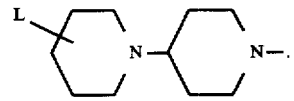

More preferred are the following Z groups:

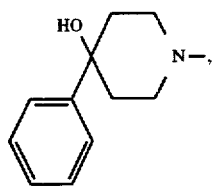

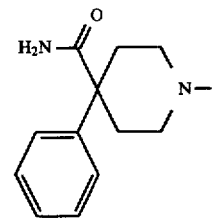

and

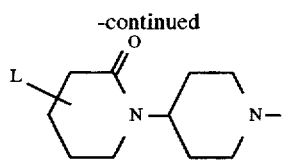

This invention also relates to the use of a compound of formula I in the treatment of asthma, cough, bronchospasm, inflammatory diseases such as arthritis, central nervous system conditions such as migraine and epilepsy, nociception, and various gastrointestinal disorders such as Crohn's disease.

In another aspect, the invention relates to a pharmaceutical composition comprising a compound of formula I in a pharmaceutically acceptable carrier. The invention also relates to the use of said pharmaceutical composition in the treatment of asthma, cough, bronchospasm, inflammatory diseases such as arthritis, migraine, nociception, and various gastrointestinal disorders such as Crohn's disease.

DETAILED DESCRIPTION

As used herein, the term "alkyl" means straight or branched alkyl chains. "Lower alkyl" refers to alkyl chains of 1–6 carbon atoms and, similarly, lower alkoxy refers to alkoxy chains of 1–6 carbon atoms.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to tetrahydrofuranyl, pyrrolidinyl, piperidinyl, morpholinyl, thiomorpholinyl and piperazinyl. $R^4$-heterocycloalkyl refers to such groups wherein substitutable ring carbon atoms have an $R^4$ substituent.

"Heteroaryl" refers to 5- to 10-membered single or benzofused aromatic rings comprising 1 to 4 heteroatoms independently selected from the group consisting of —O—, —S— and —N═, provided that the rings do not include adjacent oxygen and/or sulfur atoms. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of benzofused heteroaryl groups are indolyl, quinolyl, benzothienyl (i.e., thianaphthenyl), benzimidazolyl, benzofuranyl, benzoxazolyl and benzofurazanyl. N-oxides of nitrogen-containing heteroaryl groups are also included. All positional isomers are contemplated, e.g., 1-pyridyl, 2-pyridyl, 3-pyridyl and 4-pyridyl. $R^4$-heteroaryl refers to such groups wherein substitutable ring carbon atoms have an $R^4$ substituent.

Where $R^6$ and $R^7$ substituents form a ring and additional heteroatoms are present, the rings do not include adjacent oxygen and/or sulfur atoms or three adjacent heteroatoms. Typical rings so formed are morpholinyl, piperazinyl and piperidinyl.

In the above definitions, wherein variables such as $R^6$, $R^7$, $R^8$, $R^9$, $R^{13}$ and $R^{15}$ are said to be independently selected from a group of substituents, we mean that $R^6$, $R^7$, $R^8$, $R^9$, $R^{13}$ and $R^{15}$ are independently selected, but also that where an $R^6$, $R^7$, $R^8$, $R^9$, $R^{13}$ or $R^{15}$ variable occurs more than once in a molecule, those occurrences are independently selected (e.g., if $R^4$ is —$OR^6$ wherein $R^6$ is methyl, X can be —$N(R^6)$— wherein $R^6$ is ethyl). Similarly, $R^4$ and $R^5$ can be independently selected from a group of substituents, and where more than one $R^4$ and $R^5$ are present, the substitutents are independently selected; those skilled in the art will recognize that the size and nature of the substituent(s) will affect the number of substituents which can be present.

Compounds of the invention can have at least one asymmetrical carbon atom and therefore all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods well known to those skilled in the art. Following are typical procedures for preparing various compounds; the skilled artisan will recognize that other procedures may be applicable, and that the procedures may be suitable modified to prepare other compounds within the scope of formula I.

Procedure A:

Compounds of formula I wherein X is —C(O)—, —O—, —S(O)$_e$—, —C(O)N($R^6$)—, —OC(O)N$R^6$—, —OC(═S)N$R^6$—, —C(═NO$R^6$)—, —S(O)$_2$N($R^6$)— or —OC(O)—, Q is $R^5$ phenyl, b$_1$ is 1 or 2, and the remaining variables are as defined above, can be prepared as shown in the following reaction scheme:

Step 1:

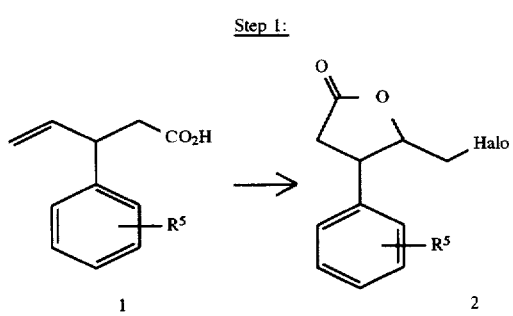

In step 1, compound 1, wherein $R^5$ is as defined above, is treated with a halogenating agent such as $I_2$ or N-bromosuccinimide in an organic solvent such as $CH_3CN$, THF or DMF at a temperature in the range of 0° to 25° C. to give the halolactone 2.

Step 2:

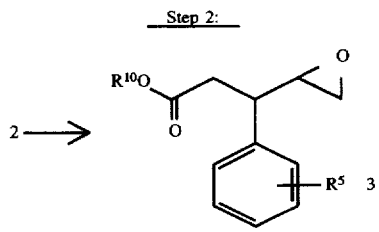

In step 2, compound 2 is dissolved in an alcohol $R^{10}OH$ wherein $R^{10}$ is preferably methyl. A base such as $Cs_2CO_3$ or $Na_2CO_3$ is added and the mixture stirred at a temperature range of 0° to 50° C. to give the epoxide 3.

Alternatively, a lower alkyl ester of 1 can be epoxidized by a suitable epoxidizing agent such as dimethyl dioxirane or m-CPBA to obtain a compound of formula 3.

Step 3:

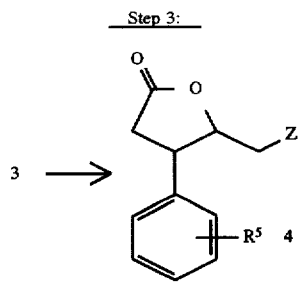

In step 3, a solution of epoxide 3 in an alcohol such as $CH_3OH$, $CH_3CH_2OH$, or more preferably $CF_3CH_2OH$, is treated with a secondary amine Z nucleophile where $R^4$ is as defined above, at 0° to 90° C. to give the lactone 4.

Step 4:

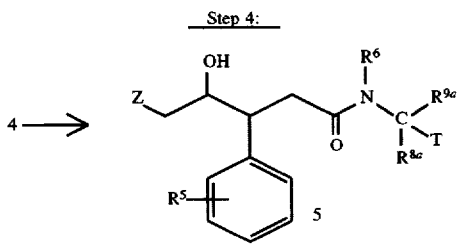

For compounds where X is —C(O)N($R^6$)— and $b_1$ is 1, lactone 4 is treated with the corresponding dialkyamine —N($R^6$)C($R^{9a}$)($R^{8a}$)-T in an alcohol such as $CH_3OH$, $CH_3CH_2OH$, or more preferably $CF_3CH_2OH$, at 0° to 90° C. to give the amide 5. Compounds of formula 5 can be converted to the corresponding keto compounds (wherein $A^1$ and $A^2$ together are =O) by oxidation with a suitable reagent such as pyridinium dichromate, Dess Martin reagent, Jones reagent, TPAP, or Swern oxidation; the keto compounds are converted to the corresponding oximes (compounds wherein $A^1$ and $A^2$ together are =NO$R^6$) by treatment of the keto compound with hydroxyl amine or an appropriate alkoxyl amine in pyridine at 23° C. to 80° C. Accordingly, the corresponding olefins (compounds wherein $A^1$ and $A^2$ together are =C($R^6$)($R^7$)) can be prepared from the respective keto compounds by using standard Wittig chemistry known to those skilled in the art.

Step 4a:

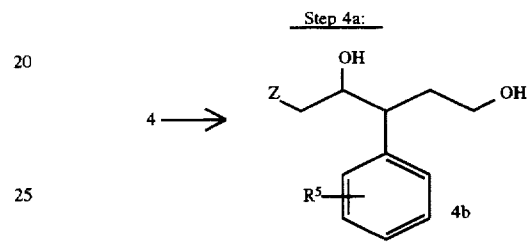

For compounds where X is —C(O)—, —O—, —S(O)$_e$—, —OC(O)N$R^6$—, —OC(=S)N$R^6$—, —C(=NO$R^6$)—, —S(O)$_2$N($R^6$)— or —OC(O)— and $b_1$ is 2, lactone 4 is treated with an appropriate reducing agent such as Dibal-H, LAH, LiBH$_4$ or NaBH$_4$, with a temperature in the range of −78° C. to 80° C. to give the corresponding diol 4b. With appropriate protection of reactive groups, compounds of formula 4b can be converted to compounds where X is —C(O)—, —O—, —S(O)$_e$—, —OC(O)N$R^6$—, —OC(=S)N$R^6$—, —C(=NO$R^6$)—, —S(O)$_2$N($R^6$)— or —OC(O)— by appropriate functional group interchange or functionalization of the terminal alcohol group. The corresponding keto compounds (compounds wherein $A^1$ and $A^2$ together are =O) may be prepared by oxidation with a suitable reagent such as pyridinium dichromate, Dess Martin reagent, Jones reagent, TPAP or Swern oxidation; synthesis of the corresponding oximes (compounds wherein $A^1$ and $A^2$ together are =NO$R^6$) are made by treatment of the keto compound with hydroxyl amine or an appropriate alkoxyl amine in pyridine at 23° C. to 80° C. Accordingly, the corresponding olefins (compounds wherein $A^1$ and $A^2$ together are =C($R^6$)($R^7$)) can be prepared from the respective keto compounds by using standard Wittig chemistry known to those skilled in the art.

Procedure B:

Compounds of formula I wherein X is —N$R^6$—, —N$R^6$C(O)—, —N($R^6$)C(=S)O—, —N($R^6$)S(O)$_2$—, —N($R^6$)C(O)O— or —N($R^6$)C(O)N($R^7$)—, Q is $R^5$ phenyl, $b_1$ is 1 and the remaining variables are as defined above, can be prepared as shown in the following reaction scheme:

Step 1:

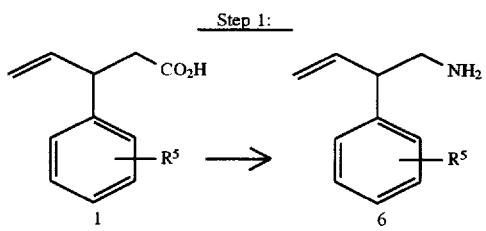

In step 1, the acid 1 is subjected to conditions typical of a Curtius rearrangement, for example; treatment with diphenylphosphoryl azide and a suitable base such as triethyl amine ($Et_3N$) in an appropriate solvent such as t-butanol. After heating to reflux, cooling and appropriate purification such as recrystallization or silica gel chromatography, the corresponding N-Boc protected amine of compound 6 is isolated. Deprotection of the Boc group by standard conditions known to those skilled in the art, such as treatment with an acid such as hydrochloric acid or trifluoroacetic acid, provides compound 6.

Step 2:

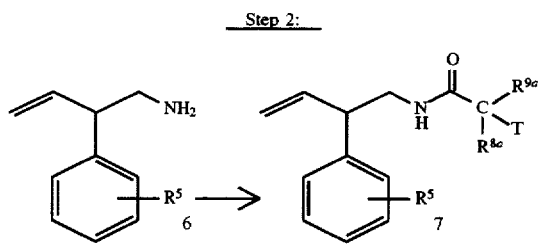

In step 2, amine 6 is acylated by standard procedures, for example by treatment with an acid chloride of the formula $T-C(R^{9a})(R^{8a})COCl$, wherein T, $R^{8a}$ and $R^{9a}$ are as defined as above, in the presence of an amine base in an inert organic solvent such as $CH_2Cl_2$ or toluene, preferably $CH_2Cl_2$, at a temperature of from $-10°$ to $50°$ C. Suitable bases include $(CH_3)_3N$, $Et_3N$ and pyridine, preferably $Et_3N$. Other acylating agents such as anhydrides are also suitable. Other coupling methods known to those skilled in the art, such as EDC coupling, may also be employed. Correspondingly, for the preparation of compounds wherein X is $—N(R^6)S(O)_2—$, $—N(R^6)C(O)O—$ or $—N(R^6)C(O)N(R^7)—$, the amine is treated with the appropriate sulfonyl halide, chloroformate, or isocyanate respectively.

Step 3:

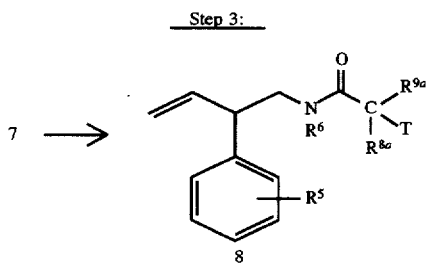

In step 2, compound 7 is treated with a base such as NaH or LDA, in an inert organic solvent such as THF, ether, DMSO or DMF, preferably THF. The resulting anion is treated with an alkylating agent $R^6L$, wherein $R^6$ is as defined above and L is a suitable leaving group such as Cl, Br, I, triflate or mesylate, to give the product of formula 8. The reactions are typically run at $0°$ to $50°$ C.

Step 4:

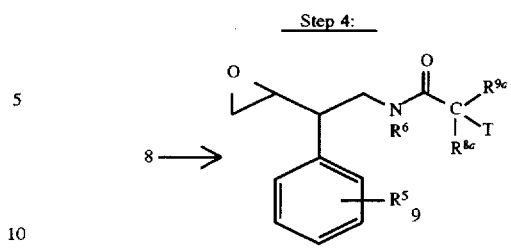

In step 3, compound 8 is oxidized to the epoxide 9 by treatment with an oxidizing agent such as dimethyl dioxirane in an inert organic solvent such as acetone at a temperature of $0°$ to $30°$ C. Other suitable oxidants can be used, for example m-CPBA in a solvent such as $CH_2Cl_2$. Suitable protective groups on $R^{9a}$, $R^{8a}$, and T on moieties susceptible to oxidation under these conditions may be necessary.

Step 5:

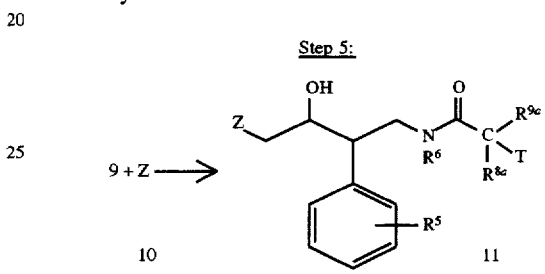

In step 5, the epoxide of formula 9 is converted to the amine of formula 11 by treating a solution of epoxide 9 in an alcohol such as $CH_3OH$, $CH_3CH_2OH$, or more preferably $CF_3CH_2OH$, with a secondary amine Z nucleophile, 10 as defined above, at $0°$ to $90°$ C. to give the amino alcohol of formula 11. Compounds of formula 11 can be converted to the corresponding keto (compounds wherein $A^1$ and $A^2$ together are $=O$) then to the corresponding oximes (compounds wherein $A^1$ and $A^2$ together are $=NOR^6$) as described above in Procedure A. Accordingly, the corresponding olefins (compounds wherein $A^1$ and $A^2$ together are $=C(R^6)(R^7)$) may be prepared from the keto compounds using standard Wittig chemistry known to those skilled in the art.

Procedure C:

Step 1:

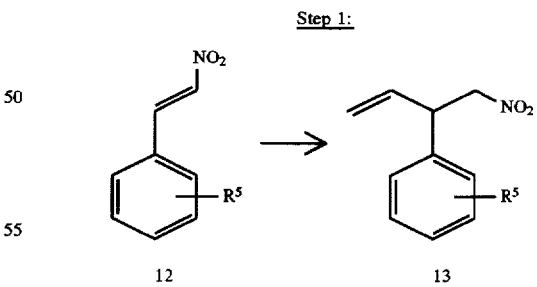

For compounds where X is a bond, $—C(O)—$, $—O—$, $—NR^6—$, $—S(O)_e—$, $—N(R^6)C(O)—$, $—C(O)N(R^6)—$, $—OC(O)NR^6—$, $—OC(=S)NR^6—$, $—N(R^6)C(=S)O—$, $—C(=NOR^6)—$, $—S(O)_2N(R^6)—$, $—N(R^6)S(O)_2—$, $—N(R^6)C(O)O—$ or $—OC(O)—$ and $b_1$ is 1, the nitro olefin 12 is added to a mixture of a copper salt, preferably CuCN, and vinyl magnesium bromide in a suitable solvent, preferably THF, with a temperature range of $-78°$ C. to $0°$ C., to give after workup and appropriate purification the nitro product 13. This product can be reduced to give the primary amine 6 or the nitro group may be transformed to the corresponding carboxylic acid via a standard Nef reaction, then to the primary alcohol with functional group transformations known to those skilled in the art. Such compounds can be converted to compounds where X is —C(O)—, —O—, —S(O)$_e$—, —OC(O)NR$^6$—, —OC(=S)NR$^6$—, —C(=NOR$^6$)—, —S(O)$_2$N(R$^6$)— or —OC(O)— by appropriate functional group interchange or functionalization of the terminal alcohol group. The corresponding keto compounds (i.e., compounds wherein A$^1$ and A$^2$ together are =O) may be prepared by oxidation with a suitable reagents such as pyridinium dichromate, Dess Martin reagent, Jones reagent, TPAP, or Swern oxidation; synthesis of the corresponding oximes (i.e., compounds wherein A$^1$ and A$^2$ together are =NOR$^6$) are made by treatment of the keto compound with hydroxyl amine or an appropriate alkoxyl amine in pyridine at 23° C. to 80° C. Accordingly, the corresponding olefins (compounds wherein A$^1$ and A$^2$ together are =C(R$^6$)(R$^7$)) can be prepared from the respective keto compounds by using standard Wittig chemistry known to those skilled in the art.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| >NH | >NCOalkyl, >NCObenzyl, >NCOphenyl, >NCH$_2$OCH$_2$CH$_2$Si(CH$_3$)$_3$, >NC(O)OC(CH$_3$)$_3$, >N-benzyl, >NSi(CH$_3$)$_3$, >NSi(CH$_3$)$_2$—C(CH$_3$)$_3$ |
| —NH$_2$ | phthalimide (—N(CO)$_2$) |
| —OH | —OCH$_3$, —OCH$_2$OCH$_3$, —OSi(CH$_3$)$_3$, —OSi(CH$_3$)$_2$—C(CH$_3$)$_3$ or —OCH$_2$phenyl |

Compounds of formula I have been found to be antagonists of NK$_1$ and/or NK$_2$ and/or NK$_3$ receptors, and are therefore useful in treating conditions caused or aggravated by the activity of said receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution The pharmaceutical compositions can be prepared with conventional excipients and additives, using well known pharmaceutical formulation techniques. Pharmaceutically acceptable excipients and additives include non-toxic and chemically compatibile fillers, binders, disintegrants, buffers, preservatives, anti-oxidants, lubricants, flavorings, thickeners, coloring agents, emulsifiers and the like.

The daily dose of a compound of formula I for treating asthma, cough, bronchspasm, inflammatory diseases, migraine, nociception and gastrointestinal disorders is about 0.1 mg to about 20 mg/kg of body weight per day, preferably about 0.5 to about 15 mg/kg. For an average body weight of 70 kg, the dosage range is therefore from about 1 to about 1500 mg of drug per day, preferably about 50 to about 200 mg, more preferably about 50 to about 500 mg/kg per day, given in a single dose or 2–4 divided doses. The exact dose, however, is determined by the attending clinician and is dependent on the potency of the compound administered, the age, weight, condition and response of the patient.

Following are examples of preparing starting materials and compounds of formula I.

EXAMPLE 1

N-|2-(3,4-dichlorophenyl)-3-hydroxy-4-(4-hydroxy-4-phenyl-1-piperidinyl)butyl|-N-methyl benzamide

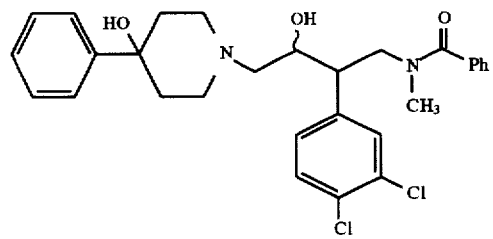

Step 1:

Cool a solution of 3-(3,4-dichlorophenyl)-2-propeneoic acid (100 g, 461 mmol) in dry DMF (500 mL) to 0° C. and treat with Cs$_2$CO$_3$ (100 g, 307 mmol, 0.66 eq). Stir the resulting off-white slurry for 15 min, then add CH$_3$I (33 mL, 530 mmol, 1.15 eq) via syringe. After 1 h, add additional DMF (250 mL), stir the slurry for 14 h and partition between EtOAc (1.5 L) and half saturated aqueous NaHCO$_3$ (500 mL). Separate the organic layer and extract the aqueous layer twice with EtOAc (1 L, 500 mL). Wash the combined organic layers with half saturated aqueous NaHCO$_3$ (500 mL) and water (5×500 mL), then dry (Na$_2$SO$_4$) and concentrate to obtain 105.4 g (456 mmol, 99%) of methyl 3-(3,4-dichlorophenyl)-2-propenoate as light brown needles.

Step 2:

Treat a solution of the product of Step 1 (15 g, 65 mmol) in dry THF (250 mL), kept cool in a large ambient temperature water bath, with Dibal-H (140 mL, 140 mmol, 2.15 eq) over 30 min. Stir the resulting solution for 30 min at 23° C., pour into Et$_2$O (500 mL), treat with water (5 mL), 15% NaOH (5 mL) and water (15 mL). Stir for 5 min, dilute the mixture with Et$_2$O (200 mL) and treat with 15% NaOH (15 mL). Add MgSO$_4$ to cause a colorless precipitate. Remove the aluminum salts by filtration through a course glass frit. Wash the solids with Et$_2$O (1 L) and concentrate the filtrate in vacuo to give 13.2 g (65 mmol, 99%) of 3-(3,4-dichlorophenyl)-2-propene-1-ol as an off-white solid.

Step 3:

Treat a solution of the product of step 2 (13.2 g, 65 mmol) in CH$_2$Cl$_2$ (250 mL) at 0° C. with pyridine (7.89 mL, 97.5 mmol, 1.5 eq) and dimethylaminopyridine (397 mg, 3.25 0.05 eq), followed by CH₃COCl (6.48 mL, 74.75 mmol, 1.15 eq). Allow the mixture to warm to 23° C., pour into 1M HCl (100 mL) and wash the resulting organic layer again with 1M HCl (100 mL), followed by water (5×100 mL; pH=6.5–7). Dry the organic layer (Na₂SO₄) and concentrate to obtain 15.4 g (62.9 mmol, 97%) of 3-(3,4-dichlorophenyl)-2-propene-1-ol acetate as a colorless oil.

Step 4:

Treat a solution of the product of step 3 (15 g, 61 mmol, dried by azeotropic distillation with toluene, 1×50 mL) in dry THF (250 mL) at −78° C. with chlorotriethylsilane (20.2 mL, 120 mmol, 2.0 eq) rapidly followed by the addition of potassium bis(trimethylsilyl)amide (183 mL, 91.5 mmol, 1.5 eq of 0.5M in toluene) via addition funnel over 50 min. Allow the mixture to warm to 23° C. and heat to reflux for 3 h. Gradually cool the solution overnight, then quench with saturated NH₄Cl (150 mL). Stir the resultant mixture vigorously for 3 h, treat with 1M HCl (150 mL) and then extract with Et₂O (500 mL). Extract the aqueous layer with Et₂O (400 mL), wash the combined organic layers with 5% NaOH (300 mL) and extract with 5% NaOH (8×150 mL). Cool the combined aqueous layers to 5° C. and, maintaining the temperature at 5°–10° C., carefully acidify with concentrated HCl (ca 175 mL) to pH 1. Extract the aqueous layer with CH₂Cl₂ (2×800 mL), dry (Na₂SO₄) and concentrate to give 13.4 g (54.5 mmol, 89%) of 3-(3,4-dichlorophenyl)-4-pentenoic acid as a faint yellow oil.

Step 5:

Treat a solution of the product of step 4 (13.75 g, 56 mmol, dried by azeotropic distillation with toluene, 100 mL) in dry, freshly distilled t-butanol (250 mL) with freshly distilled Et₃N (9.34 mL, 70 mmol, 1.25 eq) followed by diphenylphosphoryl azide (15.1 mL, 70 mmol, 1.25 eq). Heat the resulting solution to reflux for 24 h, cool and concentrate in vacuo. Treat the resultant product with toluene (100 mL), concentrate (2 x), dissolve in hexane:EtOAc (1:1) and filter through a pad of silica gel (4×10 cm), eluting with hexane:EtOAc (1:1) (1 L). Concentrate the filtrate to obtain 20.7 g of crude 1,1-dimethylethyl-[2-(3,4-dichlorophenyl)-3-butenyl] carbamate.

Step 6:

Treat a solution of the product of step 5 (5.32 g of ca 88% pure, 14.8 mmol) in CH₂Cl₂ (100 mL) with trifluoroacetic acid (10 mL) and stir for 2 h at 23° C. Treat the mixture with heptane (50 mL) and concentrate in vacuo. Take up the resulting crude product in hexane:EtOAc (1:1) and apply to a pad of silica gel (4×10 cm) packed with hexane:EtOAc (1:1). Wash the plug with the same solvent (1 L) and then elute the desired product with CH₂Cl₂:CH₃OH (saturated with ammonia) (9:1) (1.5 L). Combine the product washes and concentrate to give 3.9 g crude amine used in the next step without further purification.

Step 7:

Cool a solution of the product of step 6 (14.8 mmol) in CH2Cl2 (100 mL) to 0° C. and treat with Et₃N (3.5 mL, 25.2 mmol, 1.5 eq) and benzoyl chloride (2.1 mL, 17.6 mmol, 1.05 eq). After 10 min, dilute the mixture to 150 mL with CH2Cl2 and wash with 10% aqueous citric acid (50 mL), water (50 mL) and aqueous saturated NaHCO3 (50 mL), then dry (Na2SO4) and concentrate. Triturate the resulting crude off-white solid with hexane (40 mL) to give 3.29 g (10 mmol, 68%, over three steps) of N-[2-(3,4-dichlorophenyl)-3-butenyl] benzamide as a colorless solid.

Step 8:

Wash a suspension of NaH (312 mg of 60% in mineral oil, 7.81 mmol, 1.25 eq) in hexane with dry pentane (2×100 mL), suspend in dry THF (30 mL) and treat with the product of step 7 (2.0 g, 6.25 mmol) at 23° C. Stir the resulting yellow suspension for 20 min at 23° C., then add CH₃I (777 μL, 12.5 mmol, 2.0 eq). After 1 h, pour the mixture onto a pad of silica gel packed with hexane:EtOAc (1:1) (500 mL) and concentrate the filtrate to give 2.1 g (6.25 mmol, >99%) of N-[2-(3,4-dichlorophenyl)-3-butenyl]-N-methyl benzamide as a light yellow liquid.

Step 9:

Treat a solution of the product of step 8 (2.1 g, 6.25 mmol) in dry CH₂Cl₂ (50 mL) with a freshly prepared solution of dimethyldioxirane in acetone (100 mL of ca 0.08M in acetone). Stir the solution for 20 h, concentrate in vacuo, azeotrope with toluene (2×75 mL) and then purify by silica gel chromatography (column: 4×16 cm; eluant: hexane:EtOAc (1:1), to obtain isomer A: 854 mg (2.44 mmol, 39%) of (trans)-N-[2-(3,4-dichlorophenyl)-2-oxiranylethyl]-N-methyl benzamide as a colorless oil; and isomer B: 1.04 g (2.98 mmol, 48%) of (cis)-N-[2-(3,4-dichlorophenyl)-2-oxiranylethyl]-N-methyl benzamide as a colorless solid (total yield 87%).

Step 10:

Treat a solution of isomer A of step 9 (201 mg, 0.574 mmol) in 2,2,2 trifluoroethanol (3 ml) with 4-hydroxy-4-phenyl piperidine (508 mg, 2.87 mmol, 5 eq). Stir the resulting light yellow solution for 24 h at 23° C., concentrate in vacuo, azeotrope with toluene (2×5 ml) and concentrate. Purify the resulting crude solid by silica gel chromatography (column: 2.5×18 cm; eluant: gradient CH₂Cl₂:CH₃OH (saturated with ammonia) (97:3) to (95:5)) to obtain 302.8 mg (0.574 mmol, >99% of the title compound as a colorless foam. HRMS (FAB, M+H⁺): m/e calc'd for [C₂₉H₃₃Cl₂N₂O₃]⁺: 527.1868, found 527.1853.

The compounds of Examples 2–4 are prepared by methods similar to those described in Example 1. For Examples 3–4, the starting material is 3-(4-methoxyphenyl)-4-pentenoic acid, prepared from octyl-3-(4-methoxy)-2-propenopate in a manner similar to the procedure described in Example 1, steps 2–4.

EXAMPLE 2

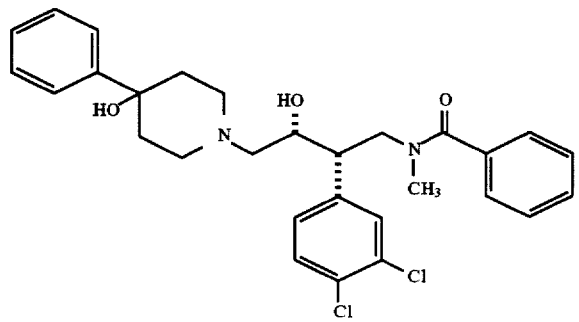

HRMS (FAB, M+H⁺): m/e calc'd for [C₂₉H₃₃Cl₂N₂O₃]⁺: 527.1868, found 527.1863. (Stereochemistry shown is relative.)

EXAMPLE 3

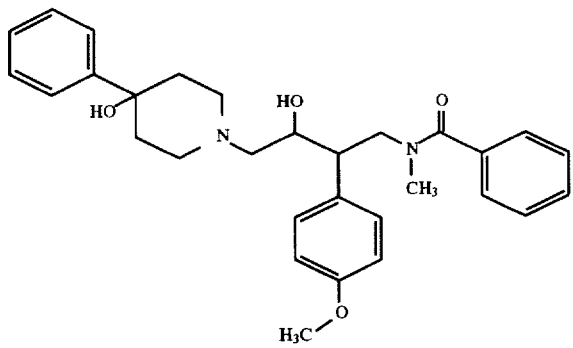

HRMS (FAB, M+H⁺): m/e calc'd for $[C_{30}H_{36}N_2O_4]^+$: 489.2753, found 489.2754.

EXAMPLE 4

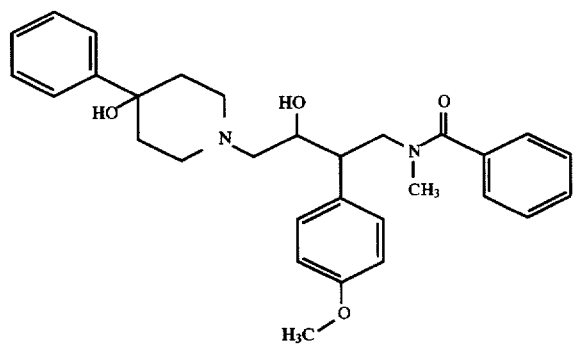

HRMS (FAB, M+H⁺): m/e calc'd for $[C_{30}H_{36}N_2O_4]^+$: 489.2753, found 489.2735.

EXAMPLE 5

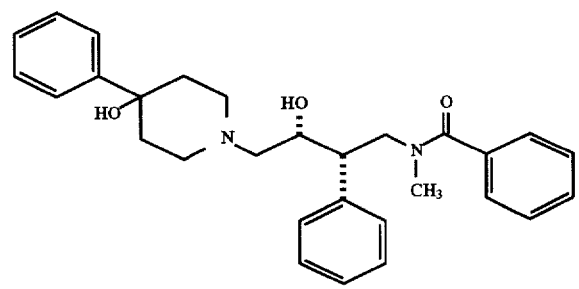

Step 1:

Cool a suspension of CuCN (3.3 g, 36.6 mmol, 1.1 eq) in dry THF under argon to −78° C. and treat with vinyl magnesium bromide (73.8 mL of 1M solution in THF, 78 mmol, 2.2 eq) dropwise over a period of 30 min. Warm the mixture to 0° C. After stirring for 10 min at 0° C., cool the solution to −20° C., stir for 10 min, then add a solution of trans-β-nitrostyrene (5 g, 33.5 mmol) in dry THF (15 mL). Stir the suspension for 1 h, then pour into a 1:2 mixture of 0.1M HCl/acetic acid (600 mL). Extract the resulting aqueous phase with CH₂Cl₂ (400 mL), wash the organic layers with water (2×300 mL), dry (Na₂SO₄) and concentrate to give 7 g of crude product. Purify by silical gel chromatography (7×16 cm, eluant: hexane/CH₂Cl₂ (3:1) (1L) gradient to (2:1)) to obtain 2.5 g (14.1 mmol, 42%) of the desired product as a light yellow liquid.

Step 2:

Shake aluminum strips (5 g) with a solution of 2% aqueous HgCl₂ (60 mL) for 1.5 min. Decant the aqueous layer, wash the foil with ethanol (2×50 mL) followed by ether (2×50 mL), and suspend in ether (50 mL)/THF (30 mL). Add the product of step 1 (2.5 g) as a solution in THF (20 mL). Add water (5 mL) and CH₃OH (5 mL) and stir the suspension for 48 h at 23° C. Filter the resulting suspension through a cake of celite (10×3.5 cm), rinsing with CH₃OH. Concentrate the filtrate to obtain 2.1 g (14.1 mol, >95%) of 2-(3,4-dichlorophenyl)-3-butenyl amine as a light yellow oil.

Step3:

Use the product of step 2 in a procedure similar to that described in Example 1, steps 7–10, to obtain the title compound (cis isomer):

HRMS (FAB, M+H⁺): m/e calc'd for $[C_{29}H_{35}N_2O_3]^+$: 459.2648, found 459.2643.

EXAMPLE 6

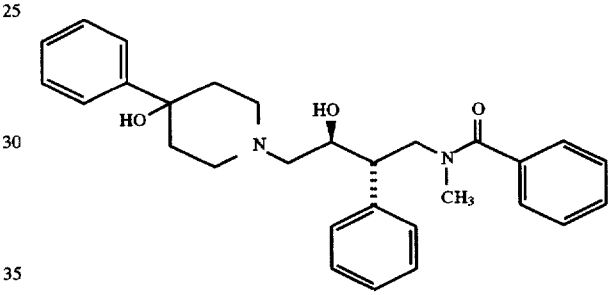

Isolate the trans isomer prepared by the process described in Example 5: HRMS (FAB, M+H⁺): m/e calc'd for $[C_{29}H_{35}N_2O_3]^+$: 459.2648, found 459.2644.

Examples 7 and 8 (diastereomers) are prepared in a similar manner to that described in Example 5 using 4-chloro-trans-β-nitrostyrene as the starting material.

EXAMPLE 7

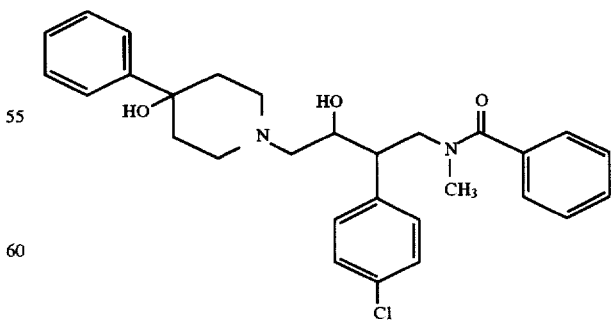

HRMS (FAB, M+H⁺): m/e calc'd for $[C_{29}H_{33}Cl_2N_2O_3]^+$: 493.2258, found 493.2261.

EXAMPLE 8

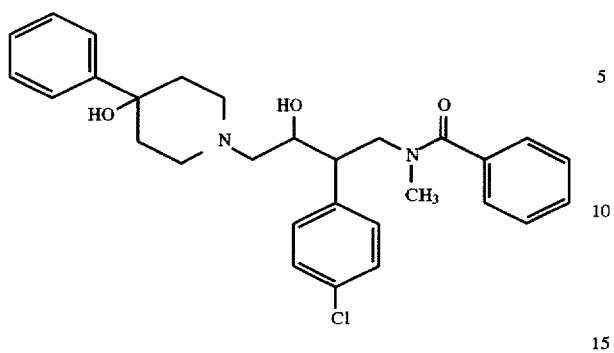

HRMS (FAB, M+H⁺): m/e calc'd for [C₂₉H₃₃ClN₂O₃]⁺: 493.2258, found 493.2270.

Examples 9 and 10 were prepared by a procedure similar to that of Example 5 using 4-methyl-trans-β-nitrostyrene as the starting material.

EXAMPLE 9

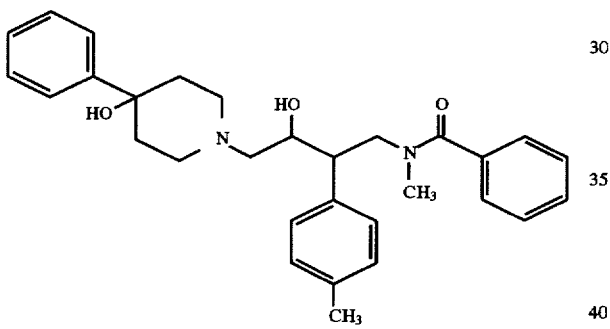

HRMS (FAB, M+H⁺): m/e calc'd for [C₃₀H₃₆N₂O₃]⁺: 473.2804, found 473.2803.

EXAMPLE 10

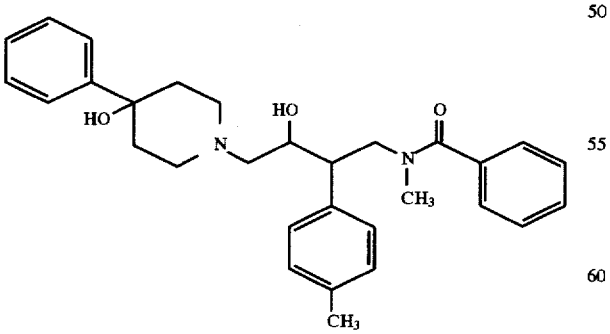

HRMS (FAB, M+H⁺): m/e calc'd for [C₃₀H₃₆N₂O₃]⁺: 473.2804, found 473.2798.

EXAMPLE 11

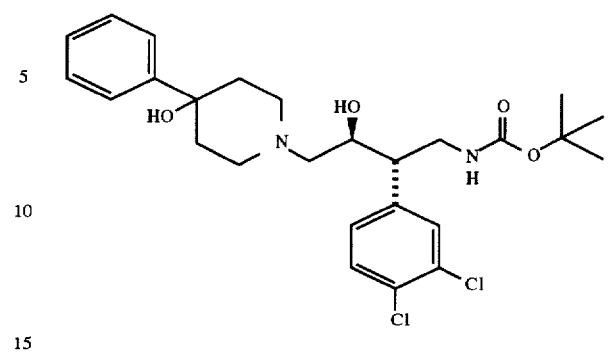

Using 1,1-dimethylethyl-[2-(3,4-dichlorophenyl)-3-butenyl] carbamate as the starting material, carry out the process described in Example 1, steps 9–10, to obtain the title compound.

HRMS (FAB, M+H⁺): m/e calc'd for [C₂₆H₃₄Cl₂N₂O₄]⁺: 509.1974, found 509.1968.

EXAMPLE 12

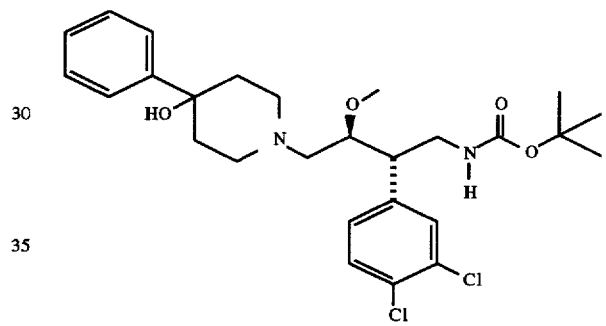

Treat the product of Example 11 in a manner similar to that described in Example 1, step 8 to obtain the title compound.

HRMS (FAB, M+H⁺): m/e calc'd for [C₂₇H₃₆Cl₂N₂O₄]⁺: 523.2130, found 523.2136.

Examples 13, 14 and 15 are prepared from Examples 1, 2 and 2, respectively, using a procedure similar to that of Example 1, step 8.

EXAMPLE 13

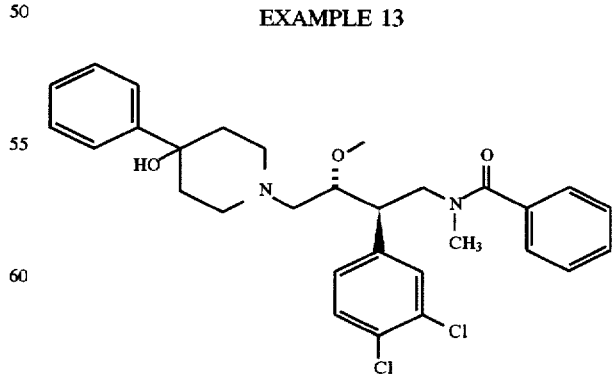

HRMS (FAB, M+H⁺): m/e calc'd for [C₃₀H₃₄Cl₂N₂O₃]⁺: 541.2025, found 541.2040.

EXAMPLE 14

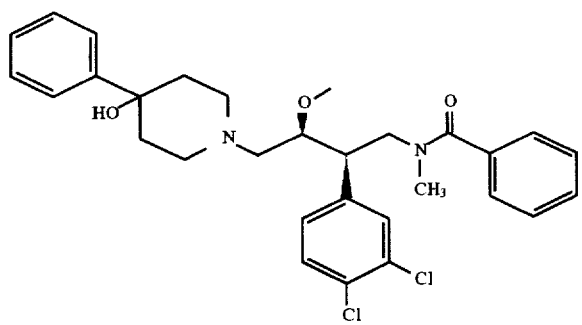

HRMS (FAB, M+H$^+$): m/e calc'd for $[C_{30}H_{34}Cl_2N_2O_3]^+$: 541.2025, found 541.2037.

EXAMPLE 15

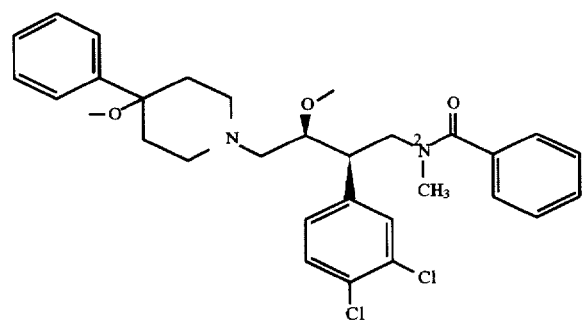

HRMS (FAB, M+H$^+$): m/e calc'd for $[C_{31}H_{36}Cl_2N_2O_3]^+$: 555.2181, found 555.2181.

EXAMPLE 16

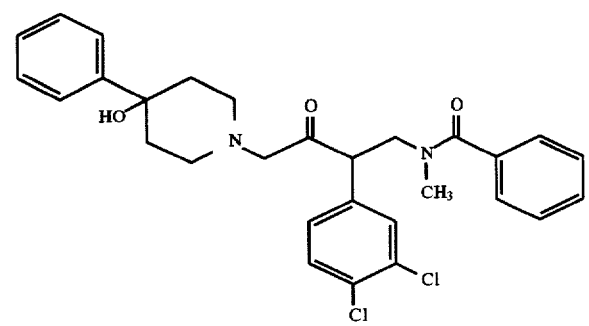

Treat the product of Example 1 in acetone with Jones reagent and stir at 0° C. for 1 h. Extract the product with CH$_2$Cl$_2$ and purify by silica gel chromatography to obtain the title compound. MS : m/e 525 (FAB, M+H$^+$).

Examples 17 and 18, regioisomers of the oxime ether, are prepared by heating the product of Example 16 in pyridine with O-methoxylamine HCl at 60° C. for 30 min. After removing the pyridine in vacuo, the crude product is purified on a silica gel column.

EXAMPLE 17

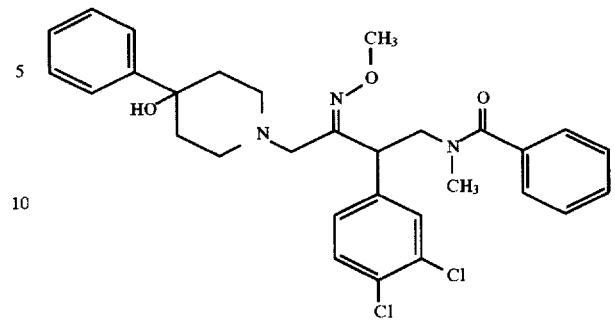

HRMS (FAB, M+H$^+$): m/e calc'd for $[C_{30}H_{33}Cl_2N_3O_3]^+$: 554.1977, found 554.1985.

EXAMPLE 18

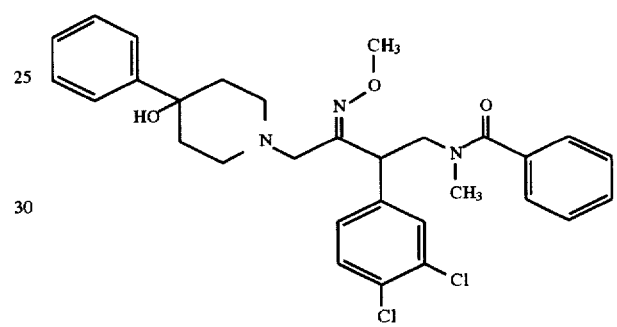

HRMS (FAB, M+H$^+$): m/e calc'd for $[C_{30}H_{33}Cl_2N_3O_3]^+$: 554.1977, found 554.1979.

Examples 19, 20, 21 and 22 are prepared from Examples 1, 2, 5 and 6, respectively, using a procedure similar to that described in Example 1, step 8, but using 3,5-(bistrifluoromethyl)benzyl bromide as the alkylhalide.

EXAMPLE 19

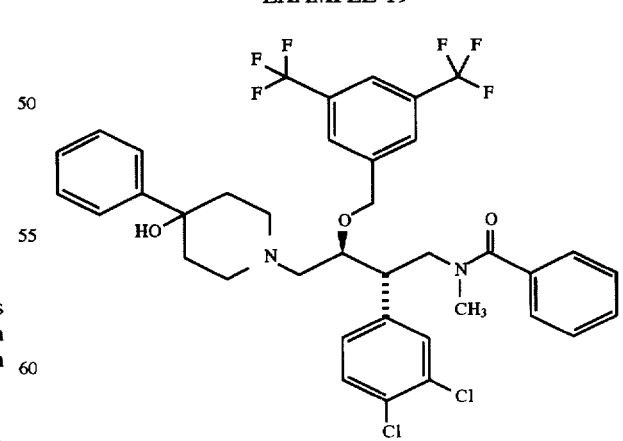

HRMS (FAB, M+H$^+$): m/e calc'd for $[C_{38}H_{37}Cl_2F_6N_2O_3]^+$: 753.2085, found 753.2058.

EXAMPLE 20

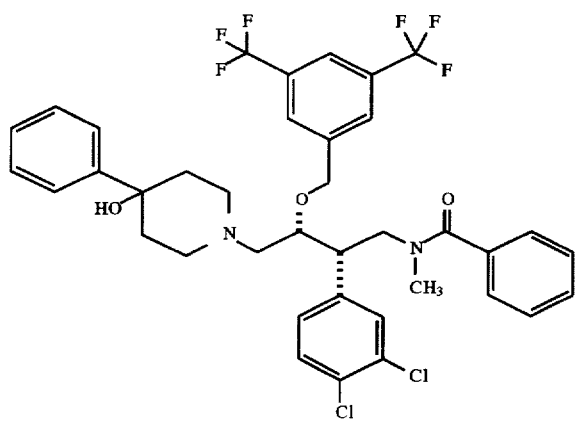

HRMS (FAB, M+H$^+$): m/e calc'd for [C$_{38}$H$_{37}$Cl$_2$F$_6$N$_2$O$_3$]$^+$: 753.2085, found 753.2065.

EXAMPLE 21

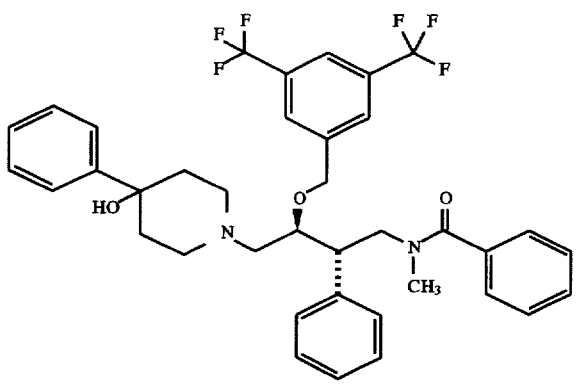

HRMS (FAB, M+H$^+$): m/e calc'd for [C$_{38}$H$_{39}$F$_6$N$_2$O$_3$]$^+$: 685.2865, found 685.2851.

EXAMPLE 22

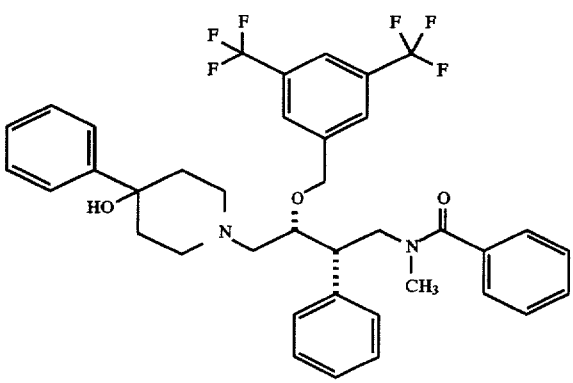

HRMS (FAB, M+H$^+$): m/e calc'd for [C$_{38}$H$_{39}$F$_6$N$_2$O$_3$]$^+$: 685.2865, found 685.2864.

Examples 23 and 24 are prepared from Examples 1 and 2, respectively, by stirring the amide in dry THF with LiAlH$_4$ for 30 min. at 23° C., partitioning between Et$_2$O, water and NaOH, removing the aluminum salts by filtration, and filtering through a plug of silica gel.

EXAMPLE 23

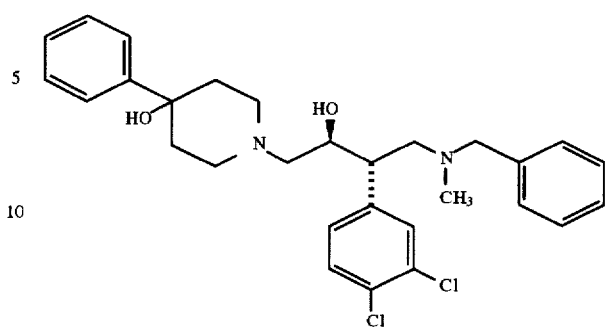

HRMS (FAB, M+H$^+$): m/e calc'd for [C$_{29}$H$_{35}$Cl$_2$N$_2$O$_2$]$^+$: 513.2076, found 513.2069.

EXAMPLE 24

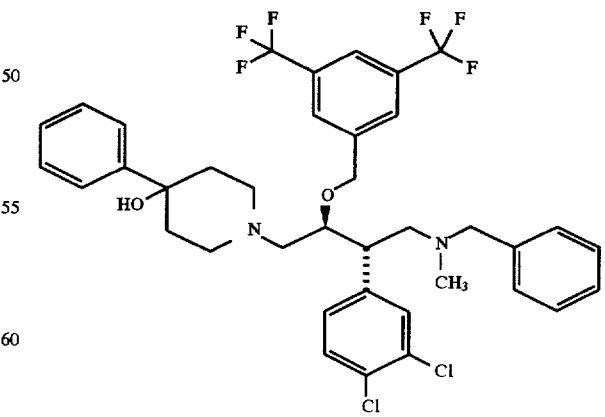

HRMS (FAB, M+H$^+$): m/e calc'd for [C$_{29}$H$_{35}$Cl$_2$N$_2$O$_2$]$^+$: 513.2076, found 513.2058.

Examples 25 and 26 were prepared from Examples 19 and 20, respectively, using a procedure similar to that used for Examples 23 and 24, using borane-dimethyl sulfide as the reductant.

EXAMPLE 25

HRMS(FAB, M+H$^+$): m/e calc'd for [C$_{38}$H$_{39}$Cl$_2$F$_6$N$_2$O$_2$]$^+$: 739.2293, found 739.2289.

EXAMPLE 26

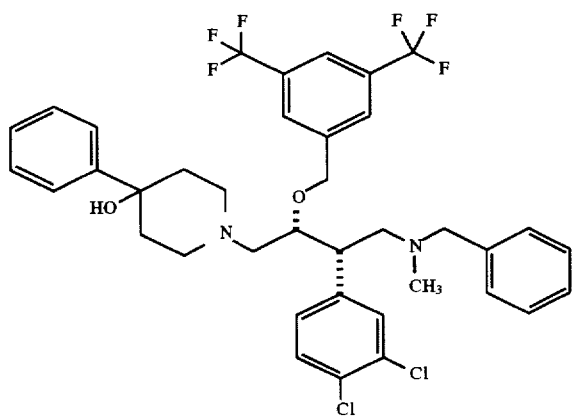

HRMS(FAB, M+H$^+$): m/e calc'd for [$C_{38}H_{39}Cl_2F_6N_2O_2$]$^+$: 739.2293, found 739.2280.

The following formulations exemplify some of the dosage of this invention. In each, the term "active compound" refers to a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|  | Total | 300 | 700 |

Method of Manufacture

Mix items Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

Sterile Powder for Injection

| Ingredient | mg/vial | mg/vial |
|---|---|---|
| Active sterile powder | 100 | 500 |

For reconstitution add sterile water for injection or bacteriostatic water for injection.

The in vitro and in vivo activity of the compounds of formula I can be determined by the following procedures.

In vitro procedure to identify NK$_1$ activity

Test compounds are evaluated for their ability to inhibit the activity of the NK$_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% O$_2$ and 5% CO$_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P potentiates the electrical field stimulated-induced contractions of the guinea pig vas deferens. In unpaired studies, all tissues (control or drug treated) are exposed to cumulative concentations of Substance P ($1\times10^{-10}$M–$7\times10^{-7}$M). Single log-concentations of the test compounds are given to separate tissues and allowed to equilibrate for 30 minutes before a Substance P concentration-response curve is generated. At least 5 separate tissues are used for each control and individual drug-concentation for every drug assay.

Inhibition of the Substance P is demonstrated by a rightward shift of its concentration-response curve. These shifts are used to determine the pA$_2$ value, which is defined as the negative log of the molar concentration of the inhibitor which would require that twice as much agonist be used to elicit a chosen response. This value is used to determine relative antagonist potency.

Isolated Hamster Trachea NK$_2$ Assay

General methodology and characterization of hamster trachea responses to neurokinin agonists as providing an NK$_2$ monoreceptor assay is found in C. A. Maggi, et al., *Eur. J. Pharmacol.* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% O$_2$–5% CO$_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6–0 silk. Baths are filled with Krebs buffer, pH 7.4, maintained at 37° C. and continuously aerated with 95% O$_2$–5% CO$_2$ gas. Tracheal rings are placed under 1.0 g initial tension and allowed a 90 min equilibration period with four 1 µM NKA challenge, wash and recovery cycles at 20 min intervals. 30 min vehicle pretreatment is followed by cumulative additions of rising doses of NKA (3 nM–1 µM final concentration, 5 min intervals between additions). The final NKA response is followed by a 15 min wash and recovery period. 30 min pretreatment with a test compound or its vehicle is followed by cumulative additions of rising doses of NKA (3 nM–10 µM final concentration if necessary, 5 min intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio $\geq 2$ at a screening concentration of 1 µM (i.e. $pA_{2\geq}=6.0$) are considered actives. Further dose response data is obtained for actives so that an apparent $pA_2$ estimate can be calculated. $pA_2$ is calculated either by estimation of $K_i$ as described by Furchgott (where $pA_2$=–Log $K_i$, R. F. Furchgott, *Pharm. Rev.* 7 [1995] 183) or by Shild Plot Analysis (O. Arunlakshana & H. O. Shild, *Br. J. Pharmacol.* 14[1959] 48) if the data is sufficient.

Effect of $NK_1$ Antagonists on Substance P-Induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 µg/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 µg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range ±2 cm $H_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range ±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 µg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L$ 100) or decreased $C_{Dyn}$ by 40% ($C_{Dyn}$40) from baseline values are obtained by log-linear interpolation of the dose response curves.

Neurokinin Receptor Binding Assay(s)

Chinese Hamster ovary (CHO) cells transfected with the coding regions for the human neurokinin 1 (NK1) of the human neurokinin 2 (NK2) receptors are grown in Dulbecco's minimal essential medium supplemented with 10% fetal calf serum, 0.1 mM non-essential amino acids, 2 mM glutamine, 100 units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended in Tris-HCl (pH7.4) containing 1 uM phsphoramidon and 4 ug/ml of chymostatin at a cell density of $30 \times 10^6$ cells/ml. The suspension is then homogenized in a Brinkman Polytron (setting 5) for 30–45 seconds. The homogenate is centrifuged at 800 x g for 5 min at 4° C. to collect unbroken cells and nuclei. The supernatant is centrifuged in a Sorvall RC5C at 19,000 rpm (44,00 x g) for 30 min at 4° C. The pellet is resuspended, an aliquot is removed for a protein determination (BCA) and washed again. The resulting pellet is stored at –80° C.

To assay receptor binding, 50 µl of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/ mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 µl of membrane (10–20 µg) containing the human NK-1 or NK-2 receptor in a final volume of 200 µl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Nonspecific binding is determined by the addition of either 1 µM of CP-99994 (NK-1) or 1 µM SR-48968 (NK-2) (both synthesized by the chemistry department of Schering-Plough Research Institute). $IC_{50}$ values are determined from competition binding curves and Ki values are determined according to Cheng and Prusoff using the experimentally determined value of 0.8 nM for the NK-1 receptor and 2.4 nM for the NK-2 receptor.

% Inhibition is the difference between the percent of maximum specific binding (MSB) and 100%. The percent of MSB is defined by the following equation, wherein "dpm" is disintegrations per minute:

$$\% \, MSB = \frac{(dpm \text{ of unknown}) - (dpm \text{ of nonspecific binding})}{(dpm \text{ of total binding}) - (dpm \text{ of nonspecific binding})} \times 100$$

It will be recognized that compounds of formula I exhibit $NK_1$, $NK_2$ and/or $NK_3$ antagonist activity to varying degrees, e.g., certain compounds have strong $NK_1$ antagonist activity, but weaker $NK_2$ and $NK_3$ antagonist activity, while others are strong $NK_2$ antagonists, but weaker $NK_1$ and $NK_3$ antagonists. While compounds with approximate equipotency are preferred, it is also within the scope of this invention to use compounds of with unequal $NK_1/NK_2/NK_3$ antagonist activity when clinically appropriate.

Using the test procedures described above, the following data were obtained for representative compounds of formula I:

| Ex. No. | % Inhibition of $NK_1$ at a dose of 1 µM | % Inhibition of $NK_2$ at a dose of 1 µM |
| --- | --- | --- |
| 2 | 81.0 | 88.0 |
| 12 | 9.0 | 68.0 |
| 16 | 23.0 | 96.0 |
| 18 | 1.0 | 15.0 |
| 19 | 78.0 | 18.0 |

Compounds of the present invention exhibit a range of activity: percent inhibition at a dosage of 1 µM ranges from about 1 to about 81% inhibition of $NK_1$ and/or about 1 to about 96% inhibition of $NK_2$. Preferred are compounds exhibiting greater than about 50% inhibition of $NK_1$ and about 1 to about 96% inhibition of $NK_2$; also preferred are compounds exhibiting about 1 to about 81% inhibition of $NK_1$ and greater than about 50% inhibition of $NK_2$. Also preferred are compounds exhibiting greater than about 50% inhibition of $NK_1$ and greater than about 50% inhibition of $NK_2$; of those compounds, more preferred are compounds exhibiting greater than about 75% inhibition of $NK_1$ and greater then about 75% inhibition of $NK_2$.

We claim:

1. A compound represented by the structural formula $$Z \underset{Q}{\overset{A^1 \; A^2}{\diagdown \diagup}} \underset{}{\overset{}{\diagdown}} X \underset{}{\overset{R^{9a}}{{+}C{+}_b}} T \atop R^{8a}$$

or a pharmaceutically acceptable salt thereof, wherein:

$A^1$ is —$CH_2R^6$, —$OR^6$, —$N(R^6)(R^7)$, —$S(O)_eR^{13}$, —$(C(R^6)(R^7))_{1-6}$—$OR^6$, —$(C(R^6)(R^7))_{1-6}$—$N(R^6)(R^7)$ or —$(C(R^6)(R^7))_{1-6}$—$S(O)_eR^{13}$ and $A^2$ is H, or $A^1$ and $A^2$ together are =O, =$C(R^6)(R^7)$, =$NOR^6$ or =S;

Q is $R^5$-phenyl, $R^5$-naphthyl, —$SR^6$, —$N(R^6)(R^7)$, —$OR^6$ or $R^5$-heteroaryl;

T is H, $R^4$-aryl, $R^4$-heterocycloalkyl, $R^4$-heteroaryl, $R^4$-cycloalkyl or $R^{10}$-bridged cycloalkyl;

b is 0, 1 or 2;

$b_1$ is 1 or 2;

X is a bond, —C(O)—, —O—, —$NR^6$—, —$S(O)_e$—, —$N(R^6)C(O)$—, —$C(O)N(R^6)$—, —$OC(O)NR^6$—, —OC(=S)$NR^6$—, —$N(R^6)C(=S)O$—, —C(=$NOR^6$)—, —$S(O)_2N(R^6)$—, —$N(R^6)S(O)_2$—, —$N(R^6)C(O)O$— or —OC(O)—;

$R^4$ and $R^5$ are independently 1–3 substituents independently selected from the group consisting of H, halogeno, —$OR^6$, —$OC(O)R^6$, —$OC(O)N(R^6)(R^7)$, —$N(R^6)(R^7)$, $C_{1-6}$ alkyl, —$CF_3$, —$C_2F_5$, —$COR^6$, —$CO_2R^6$, —$CON(R^6)(R^7)$, —$S(O)_eR^{13}$, —CN, —$OCF_3$, —$NR^6CO_2R^{16}$, —$NR^6COR^7$, —$NR^8CON(R^6)(R^7)$, $R^{15}$-phenyl, $R^{15}$-benzyl, $NO_2$, —$N(R^6)S(O)_2R^{13}$ or —$S(O)_2N(R^6)(R^7)$; or adjacent $R^4$ substituents or adjacent $R^5$ substituents can form a —O—$CH_2$—O— group; and $R^4$ can also be $R^{15}$-heteroaryl;

$R^6$, $R^7$, $R^8$, $R^{8a}$, and $R^{13}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl; with the proviso that when $A^1$ is $CH_2R^6$, $R^6$ is not hydrogen, or $R^6$ and $R^7$, together with the nitrogen to which they are attached, form a ring of 5 to 6 members, wherein 0, 1 or 2 ring members are selected from the group consisting of —O—, —S— and —$N(R^{19})$—;

$R^9$ and $R^{9a}$ are independently selected from the group consisting of $R^6$ and —$OR^6$, provided that when $R^9$ is OH, X is a bond, —C(O)—, —$N(R^6)C(O)$— or —C(=$NOR^6$)—;

$R^{10}$ is independently selected from the group consisting of H and $C_{1-6}$ alkyl;

$R^{15}$ is 1 to 3 substituents independently selected from the group consisting of H, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —$C(O)N(R^{10})_2$, —$S(O)_eR^{10}$, —CN, —$N(R^{10})COR^{10}$, —$N(R^{10})CON(R^{10})_2$ and —$NO_2$;

$R^{16}$ is $C_{1-6}$ alkyl, $R^{15}$-phenyl or $R^{15}$-benzyl;

$R^{19}$ is H, $C_1$–$C_6$ alkyl, —$C(O)N(R^{10})_2$, —$CO_2R^{10}$, —$(C(R^8)(R^9))_f$—$CO_2R^{10}$ or —$(C(R^8)(R^9))_u$—$C(O)N(R^{10})_2$;

f is 1–6;

u is 0–6;

Z is $$\begin{array}{c} R^{28} \\ \diagup \diagdown \\ | \quad \quad N— \\ \diagdown \diagup \\ | \\ \text{(phenyl)} \end{array}$$

and $R^{28}$ is OH, $C_1$–$C_6$ alkoxy or —$C(O)NH_2$.

2. A compound of claim 1 wherein X is —O—, —$NR^6$—, —$N(R^6)C(O)$—, —$OC(O)NR^6$— or —$N(R^6)C(O)O$—.

3. A compound of claim 1 wherein T is $R^4$-aryl or $R^4$-heteroaryl.

4. A compound of claim 1 wherein Q is $R^5$ phenyl, $R^5$-naphthyl or $R^5$-heteroaryl.

5. A compound of claim 1 wherein $A^1$ is —$OR^6$, —$N(R^6)(R^7)$, —$S(O)_eR^{13}$ or —$(C(R^6)(R^7))_{1-6}$—$N(R^6)(R^7)$ and $A^2$ is H; or $A^1$ and $A^2$ together are =O, =$C(R^6)(R^7)$ or =$NOR^6$.

6. A compound of claim 1 wherein b is 0 or 1, $b_1$ is 1, X is —$NR^6$— or —$N(R^6)C(O)$—, and $R^{8a}$ and $R^{9a}$ are independently selected from the group consisting of hydrogen, hydroxyalkyl and alkoxyalkyl.

7. A compound of claim 6 wherein T is phenyl substituted by two substituents selected from the group consisting of $C_1$–$C_6$ alkyl, halogeno, —$CF_3$ and $C_1$–$C_6$ alkoxy.

8. A compound of claim 7 wherein Q is phenyl di-substituted by halogeno, naphthyl or benzothienyl.

9. A compound of claim 8 wherein $A^1$ is —$OR^6$, —$N(R^6)(R^7)$, —$S(O)_eR^{13}$ or —$(C(R^6)(R^7))_{1-6}$—$N(R^6)(R^7)$ and $A^2$ is H; or $A^1$ and $A^2$ together are =O, =$C(R^6)(R^7)$ or =$NOR^6$.

10. A method of treating asthma, cough or bronchospasm comprising administering an effective amount of a compound of claim 1 to a mammal in need of such treatment.

11. A pharmaceutical composition comprising an neurokinin inhibitory effective amount of a compound of claim 1 in a pharmaceutically acceptable carrier.

12. A compound which is

N-|2-(3,4-dichlorophenyl)-3-hydroxy-4-(4-hydroxy-4-phenyl-1-piperidinyl)butyl|-N-methyl benzamide;

N-|3-hydroxy-4-(4-hydroxy-4-phenyl-1-piperidinyl)-2-(4-methoxyphenyl)butyl|-N-methyl benzamide;

N-|3-hydroxy-4-(4-hydroxy-4-phenyl-1-piperidinyl)-2-phenylbutyl|-N-methyl benzamide;

N-|2-(4-chlorophenyl)-3-hydroxy-4-(4-hydroxy-4-phenyl-1-piperidinyl)butyl|-N-methyl benzamide;

N-|3-hydroxy-4-(4-hydroxy-4-phenyl-1-piperidinyl)-2-(4-methylphenyl)butyl|-N-methyl benzamide;

1,1-dimethylethyl-|2-(3,4-dichlorophenyl)-3-hydroxy-4-(4-hydroxy-4-phenyl-1-piperidinyl)butyl|carbamate;

1,1-dimethylethyl-|2-(3,4-dichlorophenyl)-4-(4-hydroxy-4-phenyl-1-piperidinyl)-3-methoxybutyl|carbamate;

N-|2-(4-chlorophenyl)-4-(4-hydroxy-4-phenyl-1-piperidinyl)-3-methoxybutyl|-N-methyl benzamide;

N-|2-(3,4-dichlorophenyl)-4-(4-methoxy-4-phenyl-1-piperidinyl)-3-methoxybutyl|-N-methyl benzamide;

N-|2-(3,4-dichlorophenyl)-4-(4-hydroxy-4-phenyl-1-piperidinyl)-3-oxobutyl|-N-methylbenzamide;

N-|2-(3,4-dichlorophenyl)-4-(4-hydroxy-4-phenyl-1-piperidinyl)-3-(methoxyimino)butyl|-N-methylbenzamide; or N-|3-|[3,5-bis(trifluoromethyl)phenyl|methoxy|-2-(3,4-dichlorophenyl)-4-(4-hydroxy-4-phenyl-1-piperidiny)butyl-N-methyl benzamide;

N-|3-|[3,5-bis(trifluoromethyl)phenyl|methoxy|-4-(4-hydroxy-4-phenyl-1-piperidinyl)-2-phenylbutyl|-N-methylbenzamide;

α-|1-(3,4-dichlorophenyl)-2-|methyl(phenylmethyl)amino|ethyl|-4-hydroxy-4-phenyl-1-piperidineethanol; or 1-[2-|[3,5-bis(trifluoromethyl)phenyl|methoxy|-3-(3,4-dichlorophenyl)-4-[methyl(phenylmethyl)amino|butyl|-4-phenyl-4-piperidinol.

* * * * *